(12) United States Patent
Busza et al.

(10) Patent No.: US 11,547,344 B2
(45) Date of Patent: Jan. 10, 2023

(54) SYSTEM AND METHOD FOR POST-STROKE REHABILITATION AND RECOVERY USING ADAPTIVE SURFACE ELECTROMYOGRAPHIC SENSING AND VISUALIZATION

(71) Applicant: University of Rochester, Rochester, NY (US)

(72) Inventors: Ania Celine Busza, Rochester, NY (US); Edgar Andrés Bernal, Webster, NY (US); Kevin Andrew Mazurek, Rochester, NY (US); Shuyang Liu, Los Angeles, CA (US)

(73) Assignee: University of Rochester, Rochester, NY (US)

( * ) Notice: Subject to any disclaimer, the term of this patent is extended or adjusted under 35 U.S.C. 154(b) by 206 days.

(21) Appl. No.: 16/846,637

(22) Filed: Apr. 13, 2020

(65) Prior Publication Data

US 2020/0323460 A1     Oct. 15, 2020

Related U.S. Application Data

(60) Provisional application No. 62/832,542, filed on Apr. 11, 2019.

(51) Int. Cl.
*A61B 5/389* (2021.01)
*A61B 5/00* (2006.01)
(Continued)

(52) U.S. Cl.
CPC .............. *A61B 5/389* (2021.01); *A61B 5/316* (2021.01); *A61B 5/7267* (2013.01); *A61B 5/744* (2013.01);
(Continued)

(58) Field of Classification Search
CPC ....... A61B 5/389; A61B 5/316; A61B 5/7267; A61B 5/744; A61B 2502/09; G16H 40/63;
(Continued)

(56) References Cited

U.S. PATENT DOCUMENTS

2016/0235323 A1\*  8/2016  Tadi ..................... A61B 5/1128
2020/0069947 A1\*  3/2020  Kent .................... A61B 5/0809
2020/0121247 A1\*  4/2020  Lin ....................... A61B 5/389

OTHER PUBLICATIONS

Laver KE, Lange B, George S, Deutsch JE, Saposnik G, Crotty M. Virtual reality for stroke rehabilitation. Cochrane Database Syst Rev. Nov. 20, 2017;11(11):CD008349. doi: 10.1002/14651858. CD008349.pub4. PMID: 29156493; PMCID: PMC6485957. Pertinent pp. 6-7 (Year: 2017).\*

\* cited by examiner

*Primary Examiner* — Sean P Dougherty
*Assistant Examiner* — Alexander H Connor
(74) *Attorney, Agent, or Firm* — Patent Technologies, LLC; Robert D. Gunderman, Jr.

(57) ABSTRACT

A system and method for rehabilitation and recovery using adaptive surface electromyographic sensing and visualization is disclosed. The system uses surface electromyography (sEMG) sensors to identify signals of intent from patients with physical disabilities and then uses these signals to interact with a computer system designed to create repetitive practice in a manner that promotes neurological recovery. A machine teaming module analyses body signals picked up during patient movement attempts and converts these body signals to a visual representation of the intended movement by way of a virtual body or virtual body part displayed on a computer display, display glasses, or the like. The system thus allows for very early patient therapy, providing early benefits to rehabilitation therapy not heretofore possible.

(Continued)

The virtual reality or augmented reality environment provides a patient with very early visual reinforcement of beneficial muscle activation patterns.

21 Claims, 11 Drawing Sheets

(51) Int. Cl.
  *G16H 40/63* (2018.01)
  *G16H 50/30* (2018.01)
  *A61B 5/316* (2021.01)
(52) U.S. Cl.
  CPC ............ *G16H 40/63* (2018.01); *G16H 50/30* (2018.01); *A61B 2505/09* (2013.01)
(58) Field of Classification Search
  CPC ........ G16H 50/30; G16H 50/20; G16H 50/50; G16H 20/30
  See application file for complete search history.

Wearer Muscle Activation

EMG Analysis and Intended Limb Position Prediction

Limb Position Display to User

| Algorithm | Accuracy (for different EMG interval times) | | |
|---|---|---|---|
| | 1s | 0.5s | 0.1s |
| SVM | 93.125 | 92.125 | 89.875 |
| Decision Tree | 87.875 | 90.125 | 87.125 |
| Linear Regression | 85.875 | 83.5 | 83.125 |
| Naive Bayes | 92.125 | 90.125 | 87.875 |

FIG. 7

SYSTEM AND METHOD FOR POST-STROKE REHABILITATION AND RECOVERY USING ADAPTIVE SURFACE ELECTROMYOGRAPHIC SENSING AND VISUALIZATION

CROSS REFERENCE TO RELATED PATIENT APPLICATIONS

This application claims priority to U.S. Patent Application Ser. No. 62/832,542 filed Apr. 11, 2019 entitled "System And Method For Post-Stroke Rehabilitation And Recovery Using Adaptive Surface Electromyographic Sensing And Visualization" the entire disclosure of which is incorporated herein by reference.

STATEMENT REGARDING FEDERALLY SPONSORED RESEARCH OR DEVELOPMENT

This invention was made with Government Support under Contract #HD093427 awarded by National Institutes of Health. The government has certain rights in the invention.

BACKGROUND OF THE INVENTION

1. Field of the Invention

The present invention relates generally to patient rehabilitation, and more particularly to a system and method for post-stroke rehabilitation and recovery using adaptive surface electromyographic sensing and visualization.

2. Description of the Related Art

Nearly 800,000 people suffer brain injury from a stroke each year in the U.S. alone, and unfortunately, the incidence of stroke is increasing in the younger population. Despite considerable progress in stroke treatment, many stroke patients are left with permanent disabilities, including weakness in an arm or leg. The American Heart Association and the National Institute of Neurological Disorders and Stroke have prioritized the need for new methods for improved rehabilitation and functional outcomes post-stroke.

Previous studies suggest that repetitive exercising helps improve recovery from weakness due to stroke: however, many patients (especially those with severe weakness) do not do as many repetitions as animal studies suggest are necessary to boost new motor learning. Furthermore, during the recovery process, some patients develop abnormal muscle activation patterns which make normal movements more difficult (such as activating opposing muscle groups at the same time). It is hoped that new systems that encourage frequent muscle activation and positively reinforce desired muscle activation patterns early on in the recovery process in these patient groups may lead to improved post-stroke functional recovery. While such new systems may include physical therapy based devices and methods that focus on repetitive exercises, it is much more difficult to sense and provide feedback and stimulation to those patients that are very early in their recovery process, or those patients who have limited, non-existent, or abnormal muscle activation patterns. What is therefore needed is a system and related method or methods that allow for post-stroke rehabilitation and recover) by sensing low-level muscle activation cues and providing visualization and sense reinforcement of a patient's muscle activation efforts to increase new motor learning.

BRIEF SUMMARY OF THE INVENTION

In accordance with the present invention, there is provided a system to enable patient recovery of bodily functional capacity after onset of illness or injury, the system comprising a sensing module including at least one sensor that captures signals related to the body function in question; a signal processing module that analyzes the acquired signals and extracts relevant attributes; a human-computer interface module that Likes as input the extracted signal attributes and converts them into a computer control signal; and a rendering module that renders a simulated version of the human body function being performed in accordance with the control signal.

In one embodiment of the present invention, the sensing module comprises electromyography sensors.

In one embodiment of the present invention, the signal processing module comprises a machine learning system, a temporal filtering system, and combinations thereof.

The machine learning system may include a Markov chain, a neural network, a feedforward network, a convolutional network, a recurrent network, a temporal convolutional network, a generative network, a Hidden Markov model, a naïve Bayes classifier, a support vector machine classifier, a clustering framework, and various combinations thereof.

In one embodiment of the present invention, the rendering module comprises at least one of a display, or a virtual or an augmented reality device.

The rendering module may also, in some embodiments of the present invention, include an auxiliary content rendering module which renders external objects that interact with the simulated version of the human body function rendered by the rendering module.

In one embodiment of the present invention, the bodily functional capacity is one of a muscle motor function of a limb, for example, an arm or a leg.

In another embodiment of the present invention, the signal processing module identifies at least two types of attributes extracted from the acquired sensor signals, and assigns weights to the attributes depending on their identified type before transmitting them to the human-computer interface module.

The signal processing module may determine patient health such as strength or weakness based on the determined strength of the signals being acquired (for example, amplitude, as well as frequency, waveform attributes, and the like).

In some embodiments of the present invention, the system enters one of a normal, weak, and ON/OFF operation mode based on the determined level of strength of the patient.

The signal processing module may classify extracted attributes into categories indicating if they correspond to at least one of a healthy and weak patient class.

The signal processing module may further, in some embodiments of the present invention, identify signal attributes that are similar to desirable signal patterns and assign larger weights to these identified attributes when computing the input into the human computer interface.

Further, in some embodiments of the present invention, the signal processing module identifies signal attributes that are less desirable, and assigns smaller weights to these identified attributes when computing the input into the human computer interface. The human-computer interface module may also be configured to convert weighted attributes into a digital control signal.

The system of the present invention may also, in some embodiments, further include a patient tracking, module which assigns a proficiency score to the attributes extracted by the signal processing module, the proficiency score reflecting muscle activation intensity and qualitative assessment of muscle activation patterns.

The patient tracking module, in some embodiments of the present invention, assembles a time series signal containing current and past scores of a patient and transmits it to the rendering module which renders the time series in the form of a curve that is displayed to the patient. Other visualization formats including charts, progress bars and the like can be used.

The patient tracking module may also be configured to track the number of repetitions the patient accomplishes.

The patient tracking module may also be configured to assign a proficiency score to the attributes extracted by the signal processing module.

The patient tracking module may also be configured to provide a time series signal of current and past patient scores to a computer display.

In some embodiments of the present invention, the rendering module is configured to provide the simulated version of the human body function on a computer display in a position that corresponds to an anatomical side of a patient that is non-neglected due to stroke.

The system of the present invention may present the virtual arm model in the non-neglected field of view or side of the body (if a patient has neglect) such that patients with neglect can be encouraged to activate their neglected side.

The present invention includes a method for post-stroke rehabilitation and recovery having the steps of sensing an action or intended action of a human body with a sensor; providing an output of the sensor to a computer configured to extract attributes from the received output; converting with a computer the extracted attributes into a digital control signal; and rendering on a computer display a simulated version of the human body function using the digital control signal. The method may include the step of rendering auxiliary content along with the simulated version of the human body function. The method may also include the step of assigning weights to the extracted attributes. The method may also include the step of assigning a proficiency score to the extracted attributes. Other steps may also be included, or the steps defined herein may be modified, added to, deleted, or otherwise changed.

The present invention can farther be defined as a system for post-stroke rehabilitation and recovery having an array of sensors including at least one electromyography sensor; wherein the array of sensors is configured to receive hum an body signals indicative of human body action or intended action; a computer configured to receive a digital representation of output from the array of sensors and further configured to convert the digital representation of output into a digital control signal; and wherein the computer is configured to convert the digital control signal into a rendered simulated version of the human body action or intended action.

The foregoing has been provided by way of introduction, and is not intended to limit the scope of the invention as described by this specification, claims and the attached drawings.

BRIEF DESCRIPTION OF THE DRAWINGS

The invention will be described by reference to the following drawings, in which like numerals refer to like elements, and in which:

FIG. 7 is a table of performance of various machine learning systems;

Figure 1:
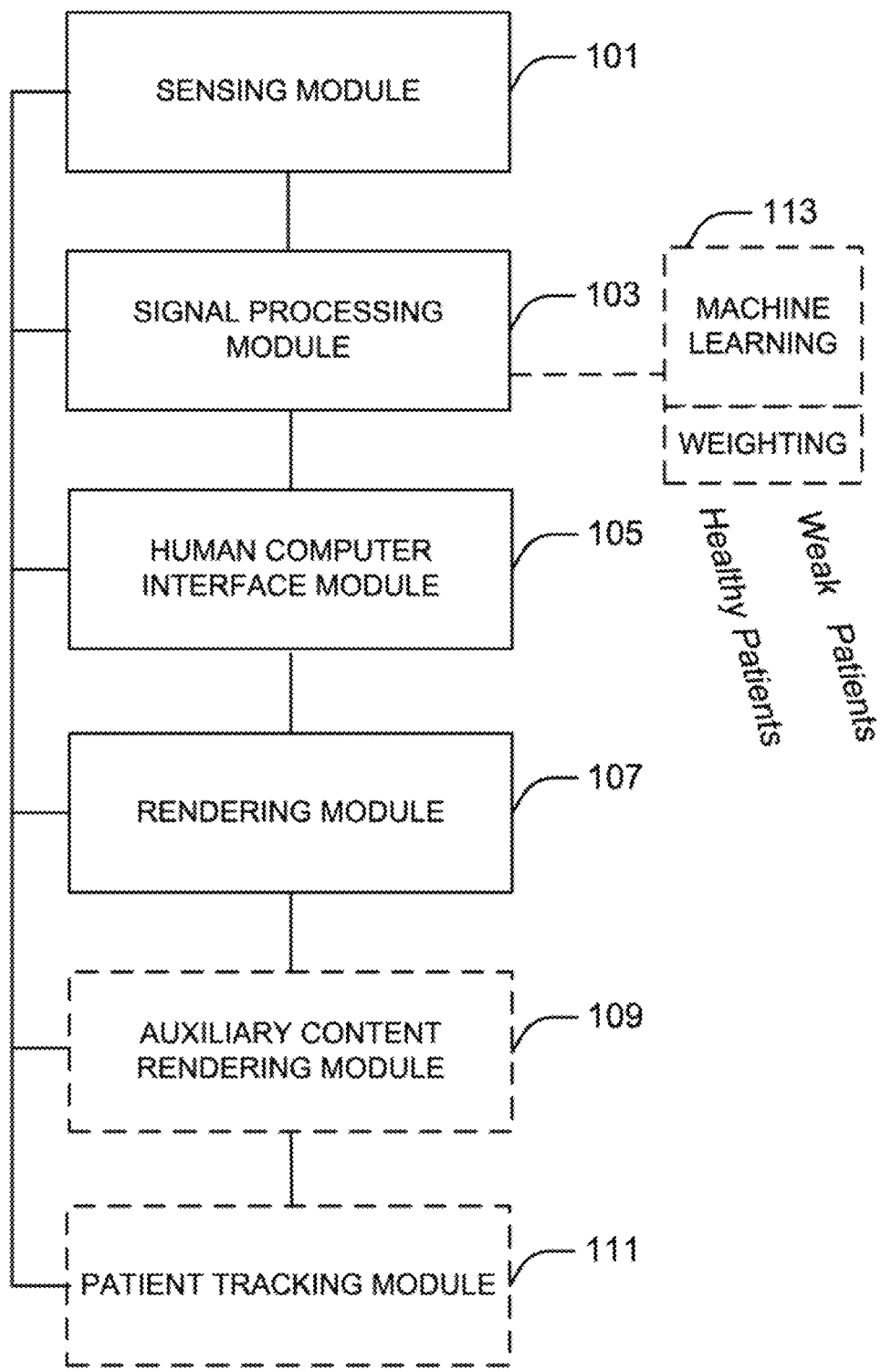
FIG. 1 is a system diagram of the present invention.

The present invention will be described in connection with a preferred embodiment; however, it will be understood that there is no intent to limit the invention to the embodiment described. On the contrary, the intent is to cover all alternatives, modifications, and equivalents as may be included within the spirit and scope of the invention as defined by this specification, claims and drawings attached hereto.

DESCRIPTION OF THE PREFERRED EMBODIMENTS

The present invention, and the various embodiments described and envisioned herein, facilitates patient rehabilitation. More specifically, the present invention improves and hastens the recovery of functional capacity after the onset of illness or injury by providing tangible visualization of a patient's muscle activation efforts through a virtual reality depiction of the patient's intended anatomical movements. The patient may be, for example, a post-stroke patient. The patient may also suffer from a variety of neurological conditions, may have orthopedic-related injuries, or have general deconditioning.

By way of example, and not limitation, a system and method of the present invention may provide a virtual arm that is controlled through a patient's muscle activation efforts. Such a virtual reality or augmented reality environment provides a patient with visual reinforcement of normal, correct, or improved muscle activation patterns. The system of the present invention combines multiple rehabilitation strategies, including biofeedback, motor imagery, increased motivation, and surface electromyographic (sEMG) sensing for training specific motor patterns, and repetitive practice.

The system of the present invention comprises: (i) a sensing module comprising one or more sensors that capture signals related to the body function in question: (ii) a signal processing module that analyzes the captured signals and extracts relevant attributes; (iii) a human-computer interface module that takes as input the captured signal attributes and converts them into a computer control signal; and (iv) a rendering module that renders a simulated version of the human body function being performed in accordance with the control signal. Optionally, (v) an auxiliary content-rendering module which adaptively renders supplementary content (that is, content not necessarily associated with the body function in question) in response to the control signal being generated. Also, optionally, (vi) a patient tracking module which extracts a proficiency score from the extracted attributes and keeps track of a patient's progress building a history of scores.

In one embodiment of the present invention, surface electromyography (sEMG) is used with surface electromyographic sensors to comprise the sensing module, with the target application being the recovery of muscle motor function after a patient has suffered a stroke. sEMG signals carry information about muscle activations in the user/patient. The acquired signals are processed in real time or near real time, and computer control signals related to the intended direction and rate of motion of the muscle being monitored are sent to a computer-based rendering engine, which in turn renders is virtual extremity (e.g., arm, leg) moving in the manner indicated by the sEMG signals. The system of the present invention detects weak muscle activity in patients with limited muscle activation or low muscle bulk, such that patients who otherwise would have limited engagement in rehabilitation therapies are encouraged to do multiple muscle activations.

Turning now to FIG. 1, a system diagram of the present invention can be seen.

The sensing module 101 comprises one or more sensors or electrodes (such as Electromyography or EMG electrodes), and may include an electromyography (EMG) machine with EMG electrodes. In one embodiment, the EMG electrodes are wireless. During rehabilitation therapy, the EMG electrodes are securely attached to the wearer's extremity using double-sided adhesive. The EMG electrodes provide information about skin surface voltage, fluctuations (related to underlying muscle activity) when configured with an appropriate current or voltage source and analog, signal amplifiers. The sensing module utilizes the analog signals received from one or more EMG electrodes and converts these analog signals into digital signals that can be further processed by way of a computer such as a PC.

The signal processing module 103 processes the resulting EMG signals and extracts movement intention attributes, thus estimating a patient's intended extremity movements from the sEMG signals collected, movements which may not be realized due to the patient's medical condition. The signal processing module may, in some embodiments of the present invention, be configured to determine health of a patient based on signal strength of the output of the sensing module. In one embodiment, the signal processing module comprises a previously trained machine learning algorithm 113 that extracts relevant features from the input EMG signals. Such features may be indicative of signal intensity and corresponding direction of intended motion. In some embodiments, of the present invention, the machine learning algorithm comprises a Markov chain, a neural network, a feedforward network, a convolutional network, a recurrent network, a temporal convolutional network, a Hidden Markov model, a naïve Bayes classifier, a support vector machine classifier, a clustering algorithm, combinations thereof, or the like. In one embodiment of the present invention, the machine learning algorithm is previously trained by processing representative sEMG signals and associated intensity and direction of intended motion labels. In some embodiments of the present invention, the signal processing module includes a temporal filtering, system in addition to, or in place of, the machine learning system.

In one embodiment of the present invention, the signal processing module, comprises a separate, previously trained machine learning algorithm that cart classify the extracted features from the input EMG signals into at least two categories, one category being indicative of attributes prevalent in signals acquired front healthy patients and one category being indicative of attributes prevalent in signals acquired from weak patients. This machine learning algorithm can similarly comprise a classifier like the ones mentioned above. In one embodiment of the present invention, the machine learning algorithm is previously trained by feeding it representative sEMG signals from healthy and from weak patients, along with the associated patient type labels. In one embodiment of the present invention, the attributes extracted from the sEMG signals may be weighted before being transmitted to the human computer interface module. In such embodiments, the weights applied to a given set of attributes can be determined based on the class to which the attribute has been determined to correspond. For example, attributes that are associated with healthy patients may be given a larger weight than those associated with weak patients so as to facilitate positive reinforcement of signals conducive to faster recovery.

The human-computer interface module 105 includes a virtual extremity controller, which receives patient movement intention attributes and converts them into control signals that are fed to the virtual extremity renderer. In cases where patients have severe weakness and produce little-to-no signal, the weighting of this mapping may be adjusted such that the virtual arm makes the correct movement even when no clear signal is detected. In one embodiment, the human-computer interface module takes the signal intensity and direction of intended motion estimates produced by the signal processing module and converts them to computer-readable signals readable by the rendering module. In some embodiments of the present invention, the human-computer interface module may perform temporal filtering of the estimates output by the signal processing module in order to avoid jitter in the rendering. In other embodiments, the signal processing module may attenuate or amplify the signal intensity conveyed by the output of the signal processing module. In some embodiments of the present invention, the human-computer interlace module is configured to convert the weighted attributes into a digital control signal that may be used, for example, in rendering.

The rendering module 107 comprises a virtual extremity renderer which maps information about intended limb (arm or leg) movement into movements of the virtual extremity. The rendering module may comprise a computer display such as a flat screen display, or a virtual reality or augmented reality device such as, for example, a headset. This simulated version of a human body function such as movement of a limb includes, for example, a limb muscle motor function. In some embodiments of the present invention, the rendering module is configured to provide the simulated version of the human body function on a computer display in a position that corresponds to an anatomical side of a patient that is non-neglected due to stroke.

The auxiliary content rendering module 109 is optional, and may render objects with which the virtual extremity can interact. Examples of such objects include external items (e.g., tools, puzzle pieces, sporting equipment, etc.) that behave in accordance with the rendered motion of the virtual extremity. The goal of the rendering of external objects is to boost motivation and promote frequent activation of the muscles, thus facilitating progress of the rehabilitation process.

The patient tracking module 111 is also optional, and tracks the progress of a given patient involved in a recovery process. To that end, the module receives the attributes extracted by the signal processing module and assigns a proficiency score to the patient based on the rated quality of the attributes. It keeps track of a patient's process by constructing a time series signal comprising all previously recorded scores, current and past, corresponding to a given patient. In some embodiments, the patient tracking module maps the signal to a curve that is passed to the rendering modules which in (urn renders it so that the patient can visualize it on a display such as a computer display. In some embodiments of the present invention, the patient tracking module is configured to track the number of repetitions of a movement, exercise, therapy, or the like, that a patient accomplishes.

In one embodiment of the present invention, the system for post-stroke rehabilitation and recovery includes an array of sensors including at least one electromyography sensor; wherein the array of sensors is configured to receive human body signals indicative of human body action or intended action; a computer configured to receive a digital representation of output from the array of sensors and further configured to convert the digital representation of output into a digital control signal; and wherein the computer is configured to convert the digital control signal into a rendered simulated version of the human body action or intended action.

Figure 2:
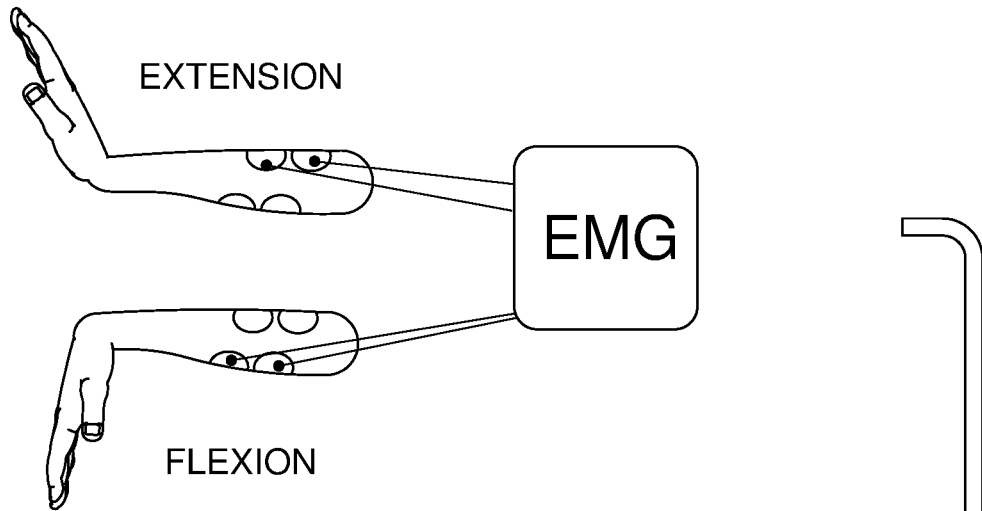
FIG. 2 is a system flow diagram of the present invention.
Figure 2:
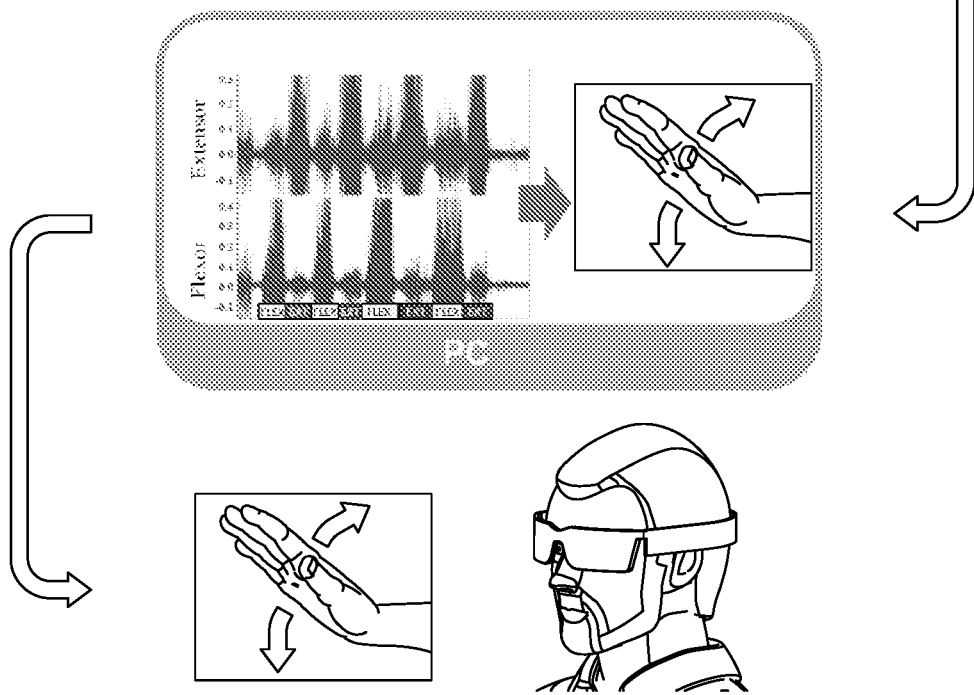
Figure 3:
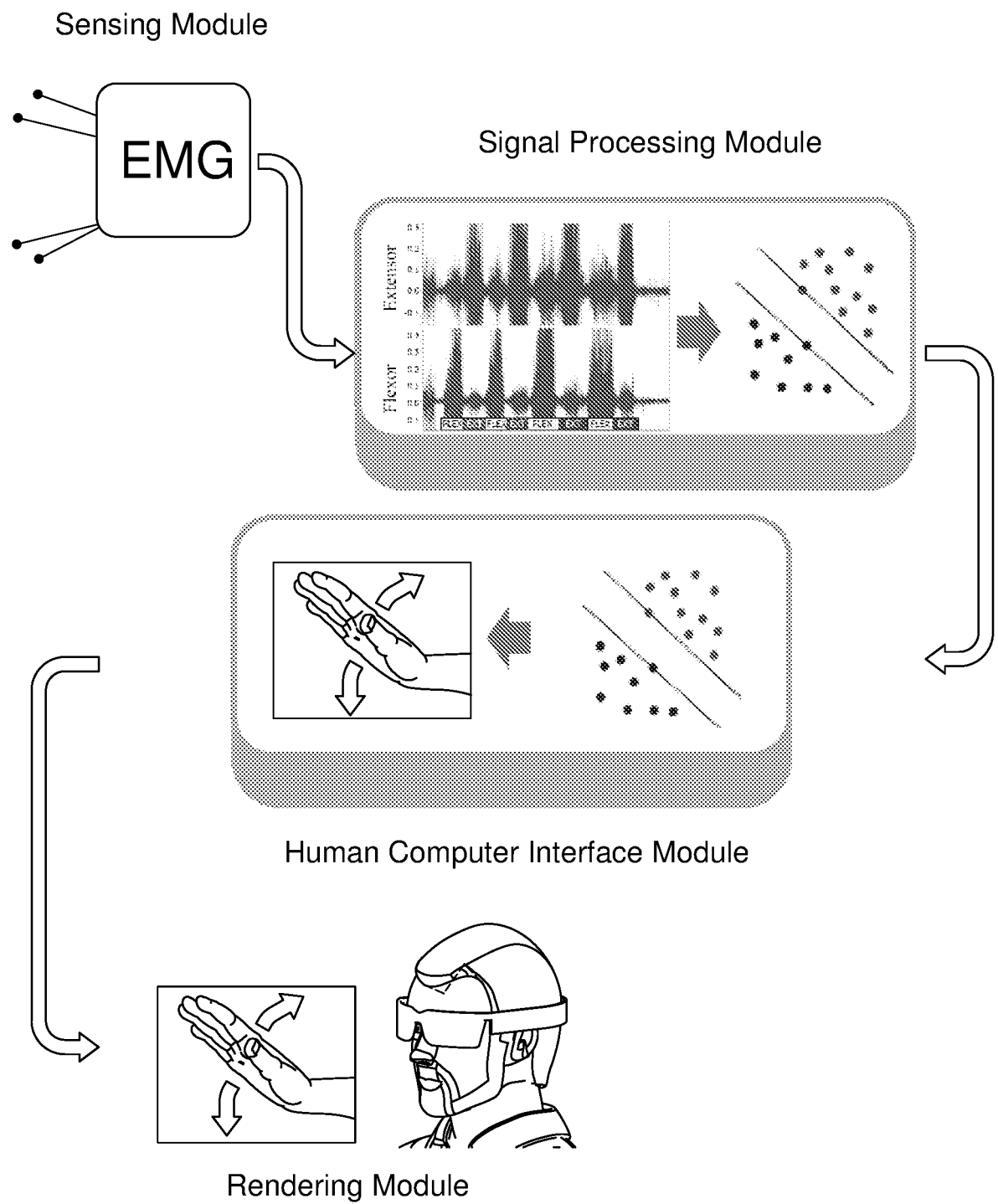
FIG. 3 is an additional system flow diagram of the present invention.

FIGS. 2 and 3 depict system level diagrams showing flow of processing. EMG sensors are secured on the body part of interest (wrist flexor muscle groups and wrist extensor muscle groups in this example). EMG fluctuations measured by the sensors are sent to a computer such as a PC via wires or a wireless signal. The EMG signals are then processed by the computer. The resulting signal is used to modify the position of a virtual body part, such as in a virtual environment with gaming features, with the environment and the moving virtual body part being displayed to the patient. In some embodiments, the display may be a computer display of any sort, including, but not limited to, wearable displays or glasses.

Figure 4:
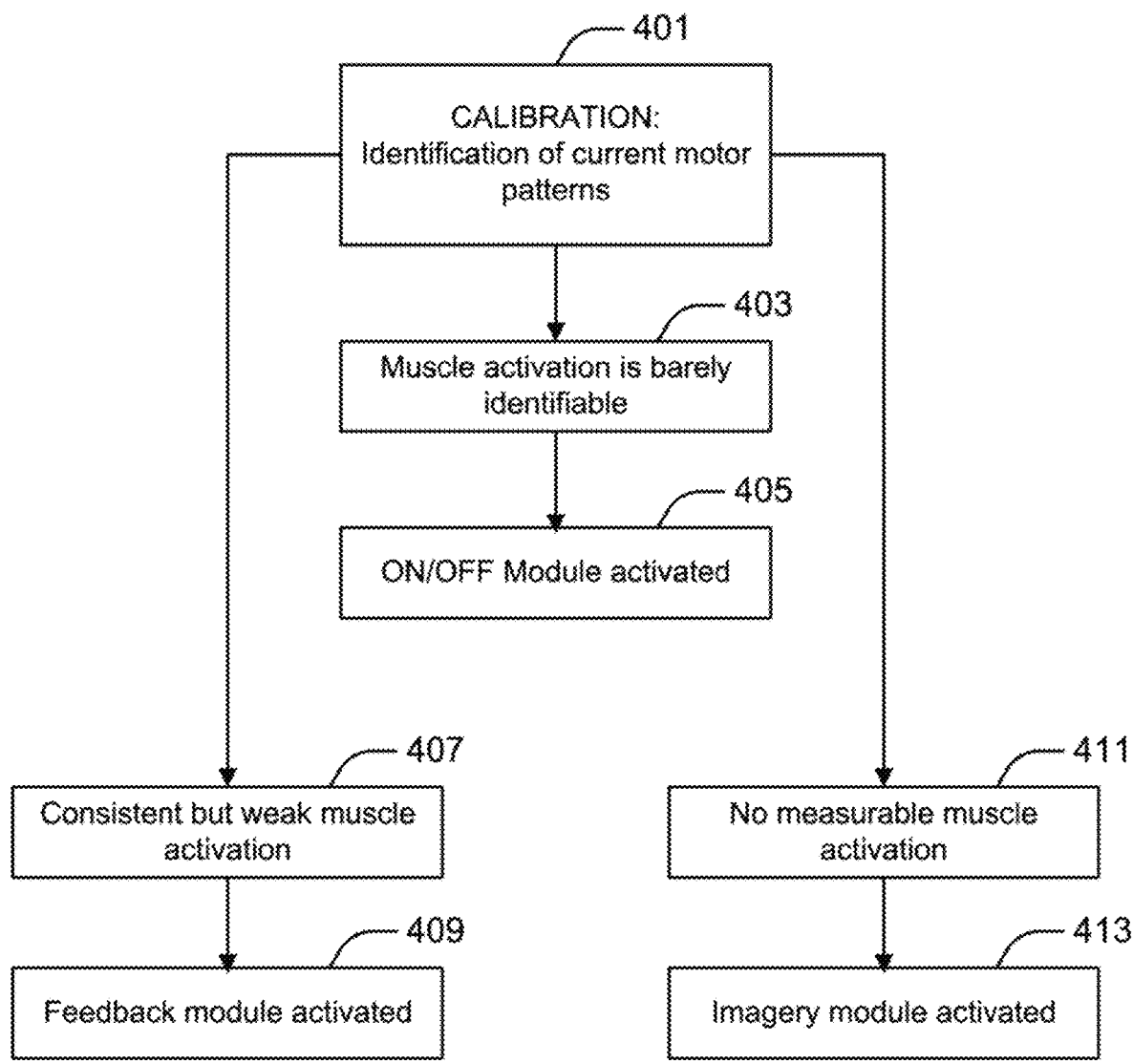
FIG. 4 is a flowchart of the present invention.
Figure 5:
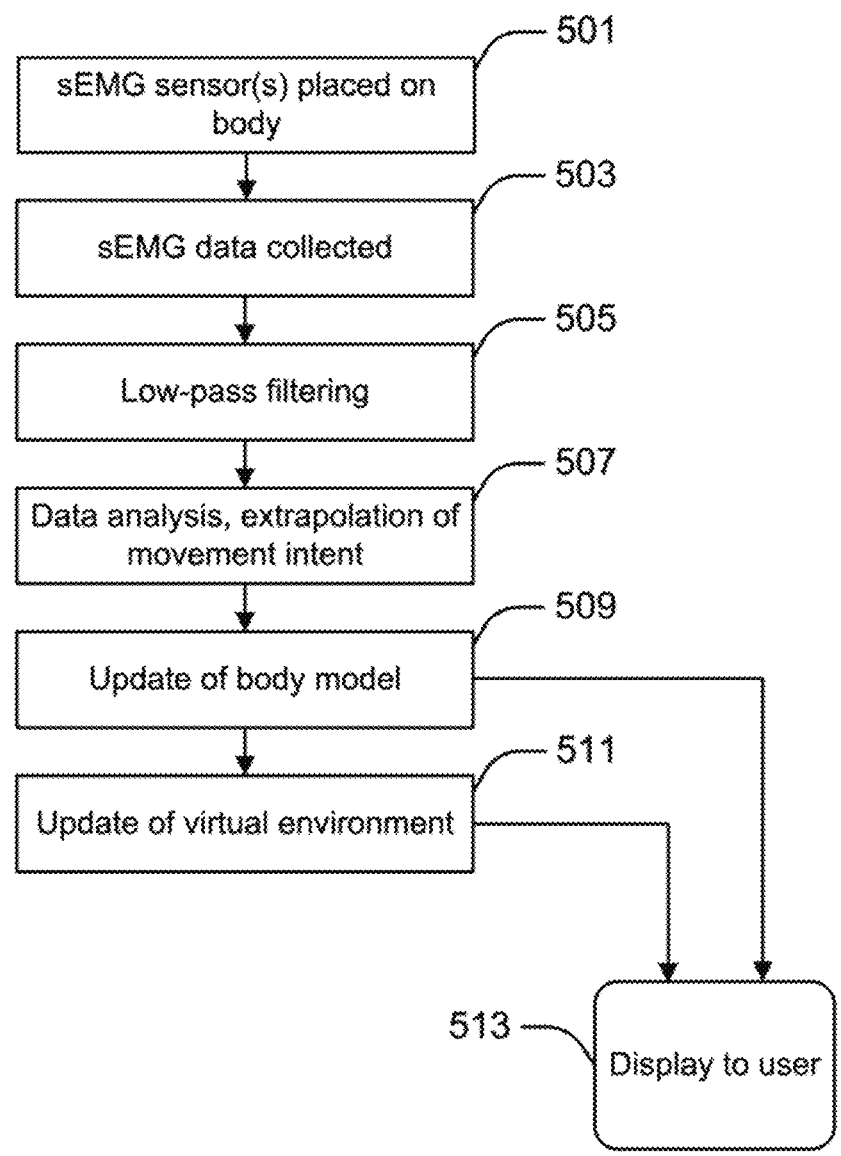
FIG. 5 is a further flowchart of the present invention.

FIGS. 4 and 5 provide representative flowcharts of how the system works to encourage repetition of specific muscle activation patterns. At the start of the session, the system is calibrated (401) to identify current motor patterns such as the level of weakness of the wearer. If the user has consistent but weak muscle activation (407), a feedback module is activated (409) where relative amounts of muscle activity are compared and desired activity patterns are positively enforced. If the user has very weak muscle activation, such that EMG activity can just barely be identified above system noise (403), an OFF/ON mode (405) is entered. In this case, any amount of activation is positively reinforced. Finally, if the user has no identifiable muscle activity or no measurable muscle activation (411), the system enters an Imagery mode (413) where the subject is still presented with visualizations of the desired movement even if at this moment they are not able to perform muscle activity to control the imagery. In one embodiment of the present invention, the imagery is passively watched by the user in the Imagery mode. In another embodiment, the user does not know if they are creating muscle activation signals sufficient for activating the system, but are still given predominantly positive feedback (for example, 70% of the time, the imagery appears to move as intended) in the Imagery mode, in order to boost motivation.

FIG. 5 is a flowchart depicting a method of the present invention. In step 501, sensors such as, for example, sEMG sensor(s) or an array of sensors are placed on the body of a patient. Data is then collected from the sensors in step 503 using the system of the present, invention described herein. Data sampling may be periodic or continuous, and may be time based or event based. To remove unwanted signals such as noise and the like, low-pass filtering is employed in step 505. The filtered data that has been collected from the sensors is then analyzed such that movement intent of the patient is determined in step 507. Movement intent may be actual muscle movement, or may be intent to move the target muscles. In subsequent step 509 the body model of the patient is updated as well as the virtual environment in step 511. The updated body model and the updated virtual environment are then displayed to the user in step 513 (typically the patient, but the display can also be directed to a clinician or the like). Thus, muscle movement intent is displayed to the patient, reinforcing correct or proper intent, and discouraging improper movement intent. This is all visualized by the patient on a computer monitor or similar display, allowing the patient to see the result of movement intent, thus providing visual reinforcement and learning through a physical therapy session or the like.

Figure 6:
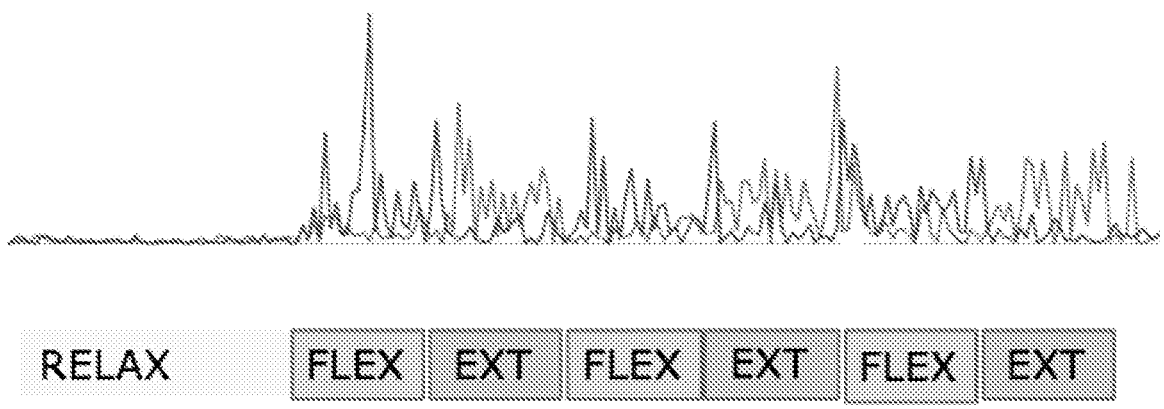
FIG. 6 depicts sample EMG signals acquired from an actual patient.
Figure 8:
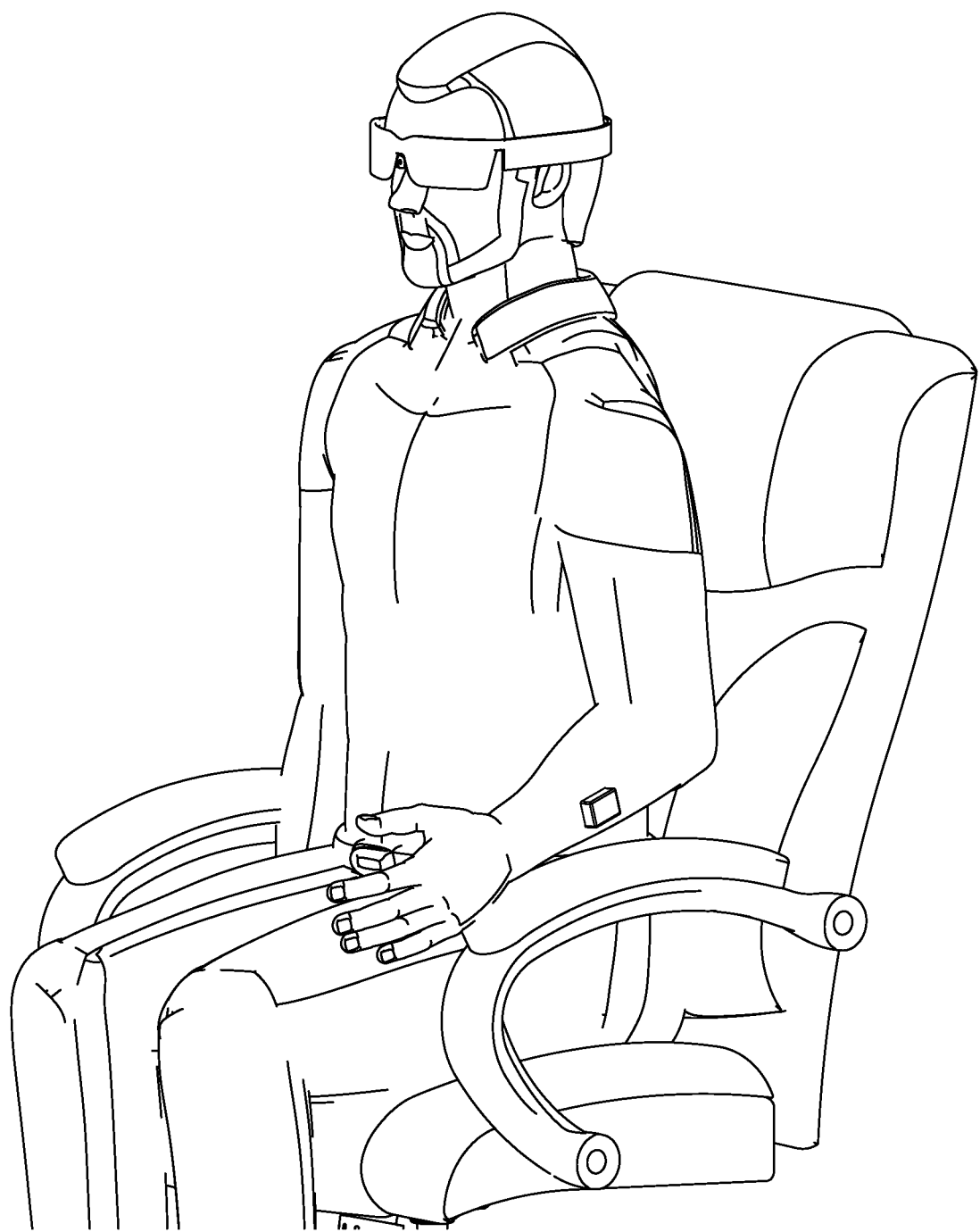
FIG. 8 shows the present invention in use with a mixed reality headset.
Figure 9:
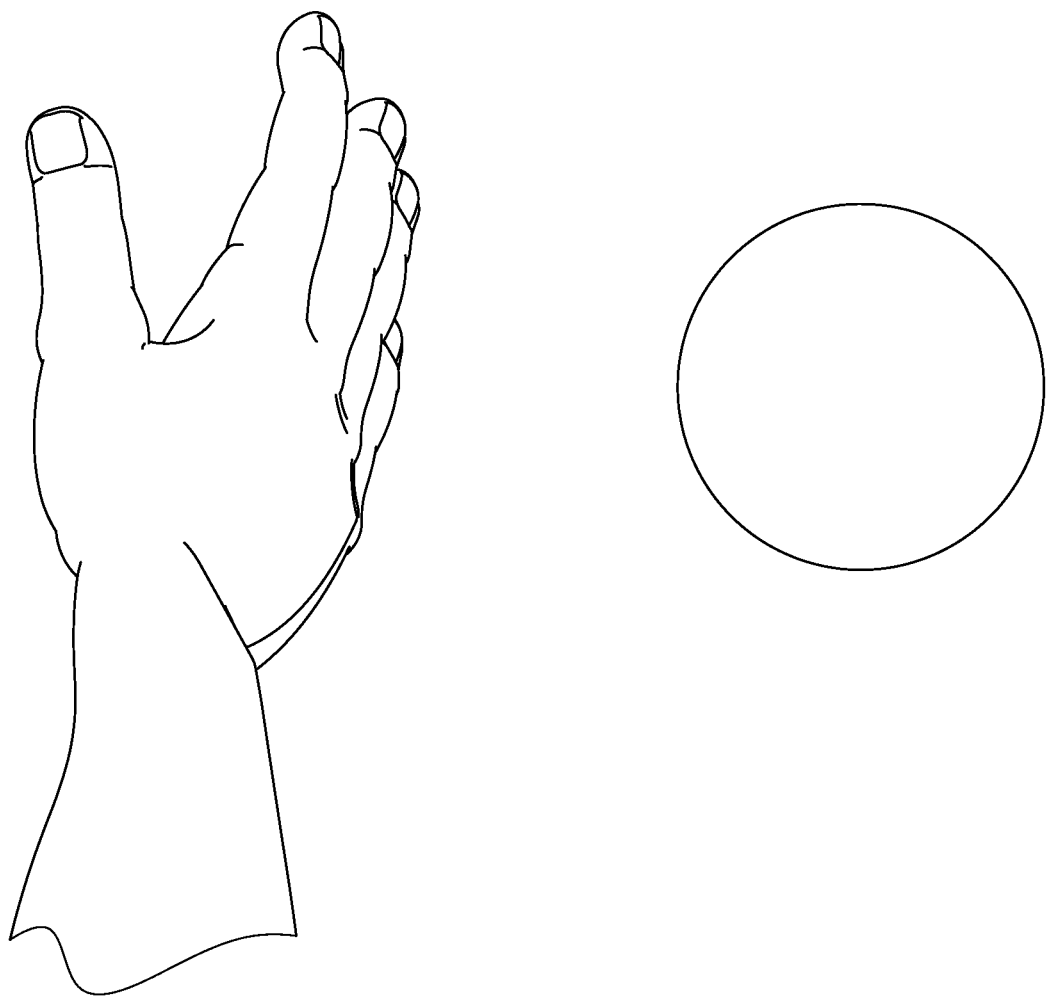
FIG. 9 depicts an example of a rendered virtual arm.

In one embodiment of the present invention, the sensing module comprises a set of sEMG electrodes that were placed over multiple patients' flexor and extensor muscle groups on their forearms. The electrical signals were collected by a Delsys EMG system with Trigno wireless electrodes. FIG. 6 illustrates sample EMG signals acquired from a real patient. The signals are color-coded, with green and orange curves being indicative of signals associated with flexor and extensor muscle groups, respectively. Signals corresponding to a total of 12 subjects were acquired; each subject was asked to flex and extend his/her arm at different points in the experiment throughout a one-minute acquisition session. The acquired signals were annotated with their corresponding label (i.e., 'flex' for flexion, 'ext' for extension and 'rest' for resting phases) as illustrated in FIG. 6. In one embodiment, the signal processing module includes a frequency domain filter which removed low-frequency noise from the acquired signals. A fraction of the labeled data was partitioned into short temporal segments of varying duration and fed to a variety of machine learning systems for training purposes. The implemented machine learning systems included a support vector machine (SVM), a decision tree, a linear regression framework and a naïve Bayes framework. The machine learning systems learned to map the input signals to the corresponding labels based on analysis of the training data. The performance of these machine learning systems was then tested on a set of previously unseen test data of the same length as the training data and also labeled. The results of this test are illustrated in FIG. 7. The results indicate that the machine learning frameworks perform well independently of the length, of the input sequence. In practice, short sequences are preferred due to decreased computational loads and processing lags or delays. The rendering module comprises a mixed reality headset Microsoft HoloLens, as illustrated in FIG. 8. A sample of the rendered virtual arm is illustrated in FIG. 9. An auxiliary content rendering module which rendered a virtual ball with which the patient was able to interact was also implemented, also as illustrated in FIG. 9. The patient was able to interact with the virtual ball in the virtual reality environment by activating his/her muscle groups in the appropriate direction.

Figure 10:
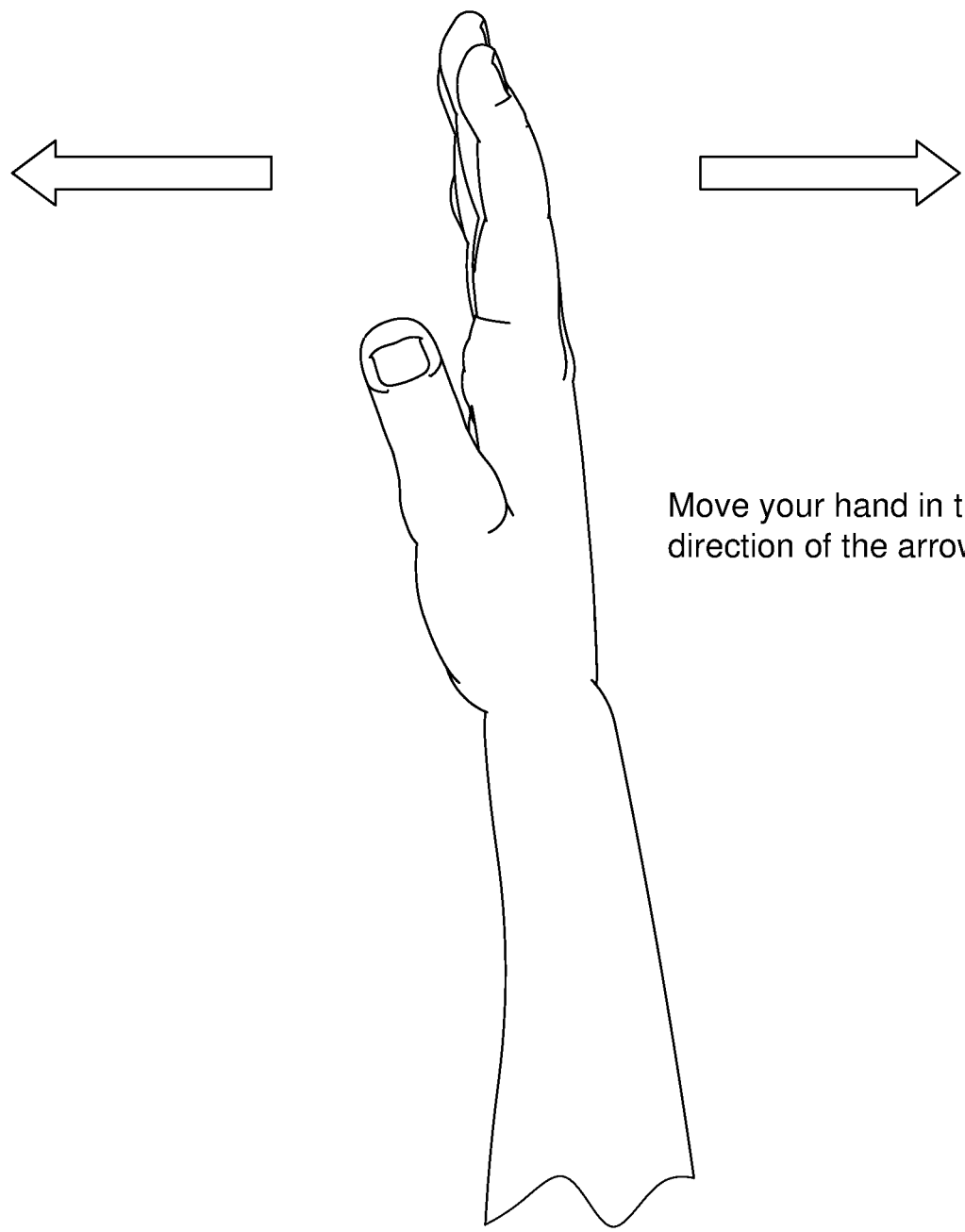
FIG. 10 depicts a virtual arm with instructions being provided to the patient.
Figure 11:
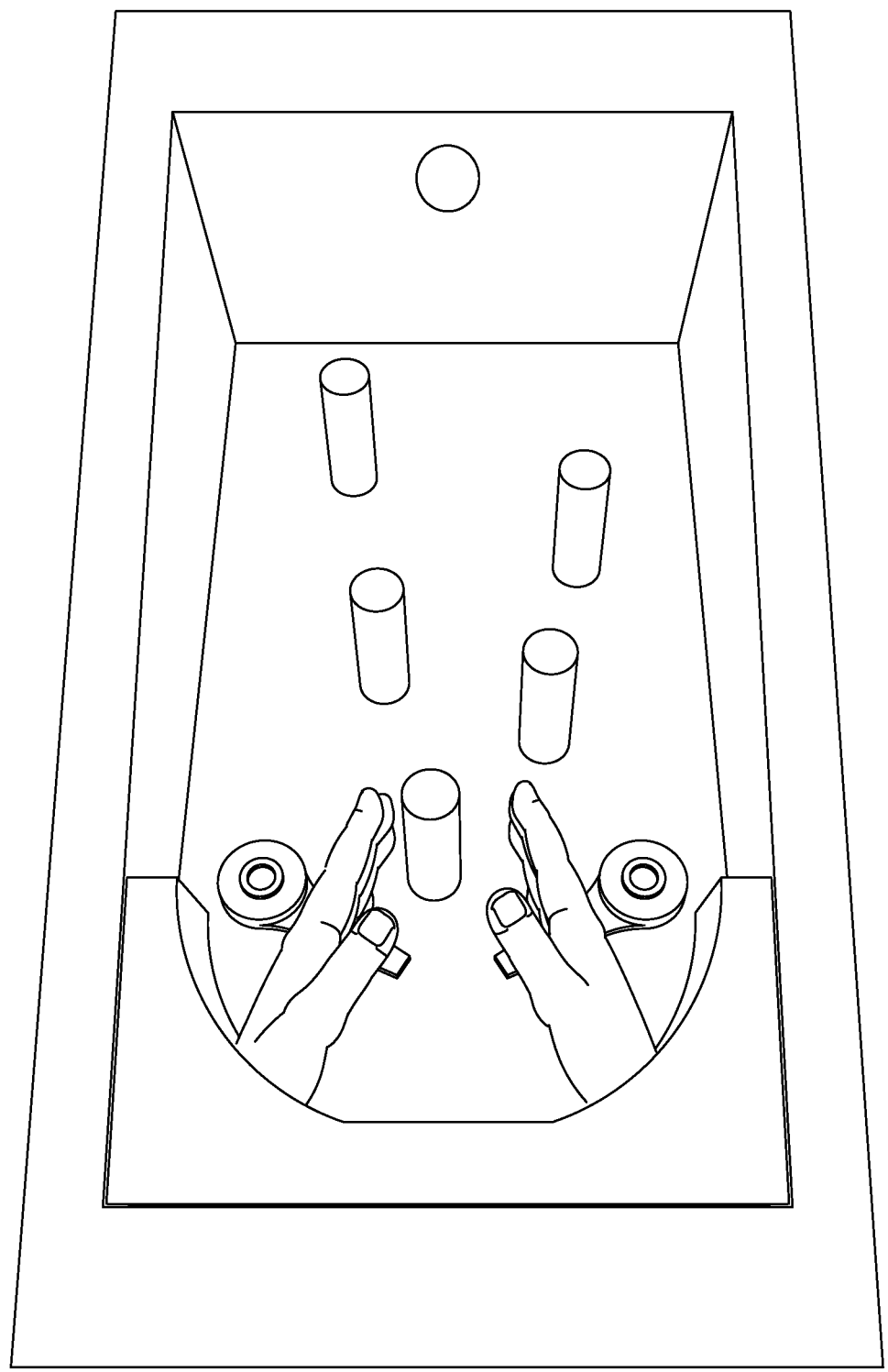
FIG. 11 depicts a virtual environment with auxiliary content rendered in addition to the virtual arm.

Further embodiments are illustrated in FIGS. 10 and 11. FIG. 10 illustrates a virtual arm with instructions being provided to the patient as to the type of extremity motion the system expects next. FIG. 11 illustrates a virtual environment with auxiliary content rendered in addition to the virtual arm. The auxiliary content comprises a pinball machine with which the subject can interact.

With the present invention, and the various embodiments described and envisioned herein, various methods may be employed. Steps include, for example, sensing an action or intended action of a human body with a sensor; providing an output of the sensor to a computer configured to extract attributes front the received output; converting with a computer the extracted attributes into a digital control, signal; and rendering on a computer display a simulated version of the human body function using the digital control signal. Additional steps may, in some embodiments include, the step of rendering auxiliary content along with the simulated version of the human body function; the step of assigning weights to the extracted attributes; the step of assigning a proficiency score to the extracted attributes; and the like.

With the system and devices of the present invention described herein, various methods become evident. These methods, which utilize, the system and devices of the present invention, are to be considered embodiments and aspects of the present invention. For example, in addition to therapy and rehabilitation of post-stroke patients, other weaknesses may also be addressed with the present invention, for example, neurological conditions, general deconditioning, orthopedic injuries, and the like. In addition, muscle groups and the conditioning or rehabilitation thereof, can be defined by some embodiments of the present invention through the use of an addressable or reconfigurable electrode array, electrode activation/deactivation instructions or functionality, and the like. Additionally, various computer interfaces may be employed to enhance, improve, expand or modify the functionality described herein.

What is claimed is:

1. A system for post-stroke rehabilitation and recovery, the system comprising:
   a computer having a processor, memory, and access to computer readable media;
   a sensing module comprising at least one sensor configured to sense action or intended action of a human body function to be rehabilitated and configured to provide an output;
   a machine learning system stored on the computer readable media and configured to receive the output of the at least one sensor and configured to extract attributes from the received output;
   a calibration computer program stored on the computer readable media where the computer program executes the step of: identifying patient motor patterns received from the machine learning system;
   a virtual extremity controller stored on the computer readable media and configured to convert the extracted attributes into a digital control signal; and
   a virtual extremity renderer stored on the computer readable media and configured to render on a computer display a simulated version of the human body function using the digital control signal;
   wherein the virtual extremity renderer positively reinforces the desired muscle activity patterns when consistent but weak muscle activation is detected by the machine learning system in the identified patient motor patterns;
   wherein the virtual extremity renderer positively reinforces any amount of muscle activity when very weak muscle activation is detected by the machine learning system in the identified patient motor patterns; and
   wherein the virtual extremity renderer presents imagery of desired muscle activity patterns when no measurable muscle activation is detected by the machine learning system in the identified patient motor patterns.

2. The system for post-stroke rehabilitation and recovery as defined in claim 1, wherein the at least one sensor is an electromyography, sensor.

3. The system for post-stroke rehabilitation and recovery as defined in claim 1, wherein the machine learning system further comprises a temporal filtering system.

4. The system for post-stroke rehabilitation and recovery as defined in claim 3, wherein the machine learning system is selected from the group consisting of a Markov chain, a neural network, a feedforward network, a convolutional network, a recurrent network, a temporal convolutional network, a generative network, a Hidden Markov model, a naïve Bayes classifier, a support vector machine classifier, a clustering framework, and combinations thereof.

5. The system for post-stroke rehabilitation and recovery as defined in claim 1, wherein the computer display is an augmented reality device.

6. The system for post-stroke rehabilitation and recovery as defined in claim 1, further comprising an auxiliary content renderer stored on the computer readable media.

7. The system for post-stroke rehabilitation and recovery as defined in claim 1, wherein the simulated version of the human body function is a limb muscle motor function.

8. The system for post-stroke rehabilitation and recovery as defined in claim 1, wherein the machine learning system is configured to determine health of a patient based on signal strength of the output of the sensing module.

9. The system for post-stroke rehabilitation and recovery as defined in claim 8, wherein the system is configured to enter one of a normal, weak, and ON/OFT operation mode based on a determined health of the patient.

10. The system for post-stroke rehabilitation and recovery as defined in claim 1, wherein the machine learning system is further configured to classify the extracted attributes into categories, wherein the categories correspond to at least one of a healthy patient class and a weak patient class.

11. The system for post-stroke rehabilitation and recovery as defined in claim 10, wherein weights are applied to the extracted attributes based on the category to which the extracted attributes correspond.

12. The system for post-stroke rehabilitation and recovery as defined in claim 11, wherein the virtual extremity controller is further configured to convert weighted attributes into a digital control signal.

13. The system for post-stroke rehabilitation and recovery as defined in claim 1, further comprising a patient tracking module stored on the computer readable media.

14. The system for post-stroke rehabilitation and recovery as defined in claim 13, wherein the patient tracking module is configured to track a number of repetitions the patient accomplishes.

15. The system for post-stroke rehabilitation and recovery as defined in claim 13, wherein the patient tracking module is configured to assign a proficiency score the attributes extracted by the signal processing module.

16. The system for post-stroke rehabilitation and recovery as defined in claim therein the patient hacking module is configured to provide a time series signal of current and past Patient scores to a computer display.

17. The system for post-stroke rehabilitation and recovery as defined in claim 1, wherein the virtual extremity renderer is configured to provide the simulated version of the human body function on a computer display in a position that corresponds to an anatomical side of a patient that is non-neglected due to stroke.

18. A method for post-stroke rehabilitation and recovery, the method comprising:
   sensing an action or intended action of a human body with a sensor;

providing an output of the sensor to a computer having a processor, memory, and access to computer readable media; wherein the computer is configured to extract attributes from the received output;

identifying, on the computer patient motor patterns from the extracted attributes:

when consistent but weak muscle activation detected in the extracted attributes, then desired muscle activity patterns are positively reinforced on a virtual extremity renderer;

when very weak muscle activation is detected in the extracted attributes, then any amount of muscle activation is positively reinforce on the virtual extremity renderer; and when no measureable muscle activation is detected in the extracted attributes, then imagery of desired muscle activity patterns are presented on the virtual extremity renderer:

converting on the computer the extracted attributes into a digital control signal; and rendering on a computer display a simulated version of the human body function using the digital control signal.

19. The method of claim 18, further comprising the step of rendering on the computer auxiliary content along with the simulated version of the human body function.

20. The method of claim 18, further comprising the step of assigning on the computer weights to the extracted attributes.

21. The method of claim 18, further comprising the step of assigning on the computer a proficiency score to the extracted attributes.

* * * * *

UNITED STATES PATENT AND TRADEMARK OFFICE
CERTIFICATE OF CORRECTION

| | | |
|---|---|---|
| PATENT NO. | : 11,547,344 B2 | |
| APPLICATION NO. | : 16/846637 | |
| DATED | : January 10, 2023 | |
| INVENTOR(S) | : Busza et al. | |

It is certified that error appears in the above-identified patent and that said Letters Patent is hereby corrected as shown below:

In the Claims

Column 9, Line 67, Claim 2, 'electromyography, sensor' should read -electromyography sensor- Column 10, Line 52, Claim 15, 'a proficiency score the attributes' should read -a proficiency score to the attributes- Column 10, Line 55, Claim 16, 'as defined in claim therein' should read -as defined in claim 13, wherein- Column 11, Line 5, Claim 18, 'identifying, on the computer' should read -identifying on the computer- Column 11, Line 7, Claim 18, 'but weak muscle activation detected' should read -but weak muscle activation is detected- Column 11, Line 13, Claim 18, 'is positively reinforce' should read -is positively reinforced- Signed and Sealed this
Twenty-eighth Day of March, 2023

Katherine Kelly Vidal
*Director of the United States Patent and Trademark Office*